(12) United States Patent
Park et al.

(10) Patent No.: US 10,921,098 B2
(45) Date of Patent: Feb. 16, 2021

(54) SYSTEM FOR DETECTING EXPLOSIVES

(71) Applicant: ISENTECH Co., Ltd., Gyeonggi-do (KR)

(72) Inventors: Inchang Park, Gyeonggi-do (KR); Jong Hyun Kim, Gyeonggi-do (KR)

(73) Assignee: ISENTECH Co., Ltd., Gyeonggi-do (KR)

( * ) Notice: Subject to any disclaimer, the term of this patent is extended or adjusted under 35 U.S.C. 154(b) by 192 days.

(21) Appl. No.: 16/111,720

(22) Filed: Aug. 24, 2018

(65) Prior Publication Data

US 2019/0101365 A1 Apr. 4, 2019

(30) Foreign Application Priority Data

Aug. 24, 2017 (KR) .................. 10-2017-0107221

(51) Int. Cl.
*G01N 33/00* (2006.01)
*F41H 11/134* (2011.01)
(Continued)

(52) U.S. Cl.
CPC ........... *F41H 11/134* (2013.01); *G01N 21/64* (2013.01); *G01N 31/227* (2013.01); *G01N 33/0057* (2013.01); *G01N 33/22* (2013.01); *G01N 21/33* (2013.01); *G01N 33/227* (2013.01); *G01N 2001/245* (2013.01)

(58) Field of Classification Search
CPC .... F41H 11/134; G01N 33/22; G01N 33/222; G01N 33/225; G01N 33/227; G01N 21/64; G01N 31/227; G01N 33/0057; G01N 21/33; G01N 2001/245; G01N 1/24; G01N 15/0205; G01N 15/1436; G01N 21/645; G01N 2201/06153
See application file for complete search history.

(56) References Cited

U.S. PATENT DOCUMENTS 6,558,626 B1 * 5/2003 Aker ....................... G01N 21/05
422/82.08
2017/0234789 A1 * 8/2017 Willis ................ G01N 21/0303
356/246

* cited by examiner

*Primary Examiner* — Xin Y Zhong
(74) *Attorney, Agent, or Firm* — Lee Hong Degerman Kang & Waimey

(57) ABSTRACT

An explosive detection system may include a suction nozzle having a suction port for introducing air containing explosive particles at one end thereof, a discharge nozzle having a discharge port for discharging air at one end thereof, a sensing block in which a detection material capable of detecting explosive particles in the air is disposed, a sensor unit for emitting light to the sensing block and outputting a sensing signal, a first guide pipe connected to the other end of the suction nozzle and guiding the air introduced through the suction nozzle to the sensing block in which the detection material is disposed, a suction force generating unit formed at the other end of the discharge nozzle and to suck air through the suction port and to provide a suction force for sucking air into the sensing block and discharging the air to a discharge port formed at one end of the discharge nozzle, a second guide pipe formed between the sensing block and the suction force generating unit and discharging the air introduced into the sensing block by the suction force generated by the suction force generating unit to the discharge port of the discharge nozzle, and a controller for determining whether explosive particles are present in the air using the sensing signal.

4 Claims, 3 Drawing Sheets

(51) Int. Cl.
*G01N 31/22* (2006.01)
*G01N 33/22* (2006.01)
*G01N 21/64* (2006.01)
G01N 21/33 (2006.01)
G01N 1/24 (2006.01)

SYSTEM FOR DETECTING EXPLOSIVES

CROSS-REFERENCE TO RELATED APPLICATION

Pursuant to 35 U.S.C. § 119(a), this application claims the benefit of earlier filing date and right of priority to Korean Patent Application No. 10-2017-0107221, filed on Aug. 24, 2017, the contents of which are hereby incorporated by reference herein in its entirety.

BACKGROUND

1. Field

The present invention relates to an explosive detection system capable of detecting explosives of nitroaromatics.

2. Related Technology

Since representative chemicals used as explosives include nitroaromatic chemicals such as trinitrotoluene (TNT) or dinitrotoluene (DNT), various methods for detecting such chemicals are being developed. Methods for detecting chemical materials contained in explosives using ion mobility spectroscopy or neutron detectors have been developed, but they have a disadvantage in that the detection time is relatively longer and the cost is higher than that of a biosensor unit. In recent years, many sensor units using nanoparticle absorption or fluorescence change have been developed, which can be easily implemented as a measuring device. This makes it possible to simply implement the measuring device, and the reaction time is short, so that it is highly likely to be applied as a real time explosive sensor.

On the other hand, DNT (dinitrotoluene) is also present in some explosives, as can be seen from the synthesis process of TNT or the decomposition process of TNT. Therefore, TNT and DNT are typical chemicals in explosives, and explosive detection devices (sensors) mainly detect these two materials. However, since TNT and DNT are solid and have very low vapor pressure, the development of receptors with stable structure in gas phase with high selectivity for detection of TNT and DNT present in the air as they are vaporized in solid explosive state may be the core of the explosives detection sensor development.

In recent years, studies on receptors capable of selectively binding DNT and TNT with high sensitivity have been progressing steadily, but there has not yet been a detection device capable of effectively detecting them.

The present invention provides an explosive detection system capable of enhancing the detection efficiency of explosive particles by increasing occupancy time of explosive particles in a sensor block made of a detection material capable of detecting particles of nitroaromatic explosive.

The present invention also provides an explosive detection system capable of increasing the accuracy in detection of explosive particles by removing humidity in the air.

The present invention provides an explosive detection system capable of reducing an error in detection of explosive particles by blocking external light.

It is to be understood, however, that the technical scope of the present invention is not limited to the above-described technical problems, and other technical problems may exist.

SUMMARY

The present invention provides an explosive detection system capable of enhancing the detection efficiency of explosive particles by increasing occupancy time of explosive particles in a sensor block made of a detection material capable of detecting particles of nitroaromatic explosive.

The present invention also provides an explosive detection system capable of increasing the accuracy in detection of explosive particles by removing humidity in the air.

The present invention provides an explosive detection system capable of reducing an error in detection of explosive particles by blocking external light.

It is to be understood, however, that the technical scope of the present invention is not limited to the above-described technical problems, and other technical problems may exist.

According to an aspect of the present invention, there is provided an explosive detection system comprising: a suction nozzle having a suction port for introducing air containing explosive particles at one end thereof; a discharge nozzle having a discharge port for discharging air at one end thereof, a sensing block in which a detection material capable of detecting explosive particles in the air is disposed; a sensor unit for emitting light to the sensing block and outputting a sensing signal; a first guide pipe connected to the other end of the suction nozzle and guiding the air introduced through the suction nozzle to the sensing block in which the detection material is disposed; a suction force generating unit formed at the other end of the discharge nozzle and to suck air through the suction port and to provide a suction force for sucking air into the sensing block and discharging the air to a discharge port formed at one end of the discharge nozzle, a second guide pipe formed between the sensing block and the suction force generating unit and discharging the air introduced into the sensing block by the suction force generated by the suction force generating unit to the discharge port of the discharge nozzle, and a controller for determining whether explosive particles are present in the air using the sensing signal.

In an embodiment of the present disclosure, the explosive detection system may further include a first light blocking block through which the first guide pipe passes, disposed between the suction nozzle and the sensor unit for blocking the introduction of external light into the sensing block.

In an embodiment of the present disclosure, the explosive detection system may further include a second light blocking block through which the second guide pipe passes, disposed between the suction force generating unit and the sensor unit for blocking the introduction of external light into the sensing block.

In an embodiment of the present disclosure, the explosive detection system may further include a first connection pipe having one end connected to the sensing block and the other end connected to the first guide pipe. Wherein a diameter of a portion connected to the suction nozzle in the first guide pipe is larger than a diameter of a portion connected to the first connection pipe.

In an embodiment of the present disclosure, the first guide pipe may be formed in a zigzag shape so as to have a width larger than the height of the sensing block.

In an embodiment of the present disclosure, the explosive detection system may further include a second connection pipe having one end connected to the sensing block and the other end connected to the second guide pipe. The second guide pipe may be formed in a zigzag shape so as to have a width larger than the height of the sensing block.

In an embodiment of the present disclosure, the sensor unit may include a light source for emitting light and a lens for collecting the light toward the sensing block. The explosive particles may be seated in the sensing block. The sensor unit may include at least two seating portions for emitting light according to the incident light and then being extinguished when the explosive particles are seated, and a light-receiving unit that receives light corresponding to the light emission or extinction state of each of the seating portions, and provides the corresponding light sensing signal to the controller.

Thus, since the multifunctional integrated module according to the present disclosure can perform different functions such as the short distance communication, the wireless power transmission, the magnetic security transmission, and the like as a single module, it can be widely applied to various portable devices and electronic devices such as various mobile devices, smart household appliances, or internet of things devices.

According to any one of the above-described objects of the present invention, it is possible to increase the detection efficiency of explosive particles by providing a detection system having a structure capable of increasing occupancy time of explosive particles in a sensor block made of a detection material capable of detecting of nitroaromatic explosives.

According to any one of the above-described objects of the present invention, the detection accuracy can be improved because the humidity in the air can be removed by compressing the air by making the diameter of the portion into which the air flows and the portion which is discharged through the sensing block different from each other.

According to any one of the above-described objects of the present invention, the explosive detection system minimizes the influence of the light in the sensing block by installing the first and second light blocking blocks which can block the external light or by implementing the structure of the first and second guide pipes in a zigzag shape, thereby reducing errors due to the influence of the light when detecting explosive particles.

DESCRIPTION OF EMBODIMENTS

Figure 1:
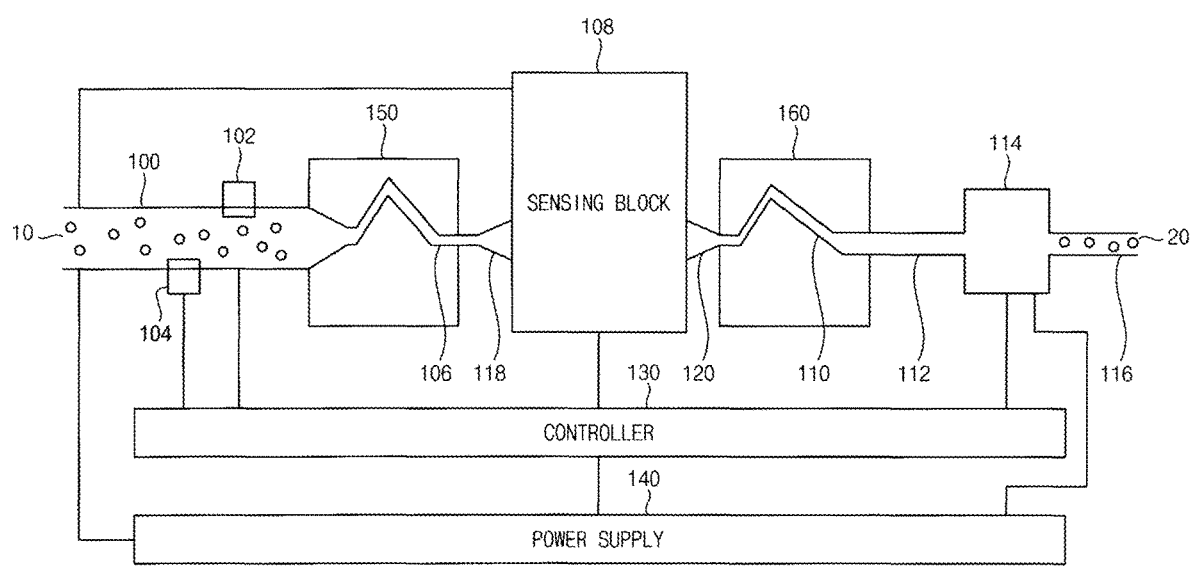
FIG. 1 is an overall configuration diagram illustrating an explosive detection system according to an embodiment of the present invention.

Various embodiments will be described more fully hereinafter with reference to the accompanying drawings, in which some embodiments are shown. The invention may, however, be embodied in many different forms and should not be construed as limited to the embodiments set forth herein. Rather, these embodiments are provided so that this description will be thorough and complete, and will fully convey the scope of the invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (for example, rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include a plurality of forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments are described herein with reference to cross-sectional illustrations that are schematic illustrations of idealized embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the face through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, it will be described an apparatus for transferring a substrate according to example embodiments with reference to the accompanying drawings.

Figure 2:
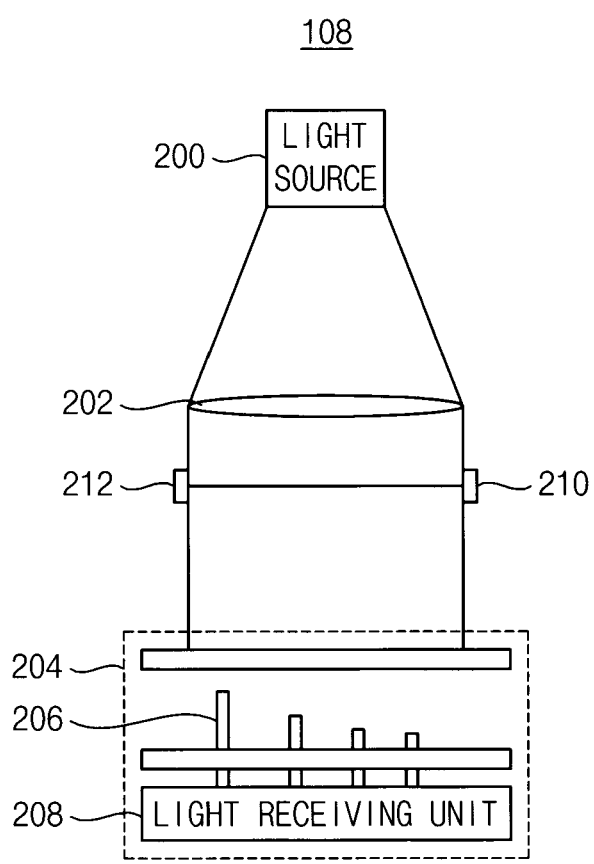
FIG. 2 is a view showing a detailed structure of a sensor unit in the explosive detection system according to the embodiment of the present invention.

FIG. 1 is an overall configuration diagram showing an explosive detection system according to an embodiment of the present invention. FIG. 2 is a detailed structure of a sensor unit in the explosive detection system according to an embodiment of the present invention.

As shown in FIG. 1, the explosive detection system according to the embodiment of the present invention is for detecting explosive particles in air introduced through a suction nozzle 100 in a sensor unit 108 to detect explosives. The explosive detection system may include a suction nozzle 100 connected to a suction port 10, a first guide pipe 106, a sensor unit 108, a second guide pipe 110, a connection nozzle 112, a suction force generation unit 114, a discharge nozzle 116 connected to a discharge port 20, first and second connection pipes 118 and 120, a controller 130 and a power supply 140.

The suction port 10 through which the air containing the explosive particles are sucked may be connected to one end of the suction nozzle 100 and the first guide pipe 106 may be connected to the other end of the suction nozzle 100.

The suction nozzle 100 may include a velocity sensor unit 102 for measuring the velocity of air and a temperature and humidity sensor unit 104 for measuring the air temperature and humidity. The velocity measurement signal sensed by the velocity sensor unit 102 and the temperature and humidity measurement signal sensed by the temperature and humidity sensor unit 104 may be input to the controller 130.

The suction nozzle 100 may suck the air by a suction force generated by the suction force generation unit 114 provided on the discharge nozzle 116. At this time, a fan may be used to generate the suction force. The sucked air may be discharged to the first guide pipe 106 connected to the end of the suction nozzle 100.

The first guide pipe 106 may have one end connected to the suction nozzle 100 and the other end connected to one side of the first connection pipe 118 connected to the sensing block 204 of the sensor unit 108.

The diameter of the other end of the first guide pipe 106 may be smaller than the diameter of the other end of the first guide pipe 106. The introduced air may be accelerated through the first guide pipe 106 and may be introduced into the sensing block (204 of FIG. 2) through the first connection pipe 118.

The first guide pipe 106 may be arranged in a zigzag shape so as to have a greater width than the height of the sensing block 204 and may be connected to the first connection pipe 118. Through the structure of the first guide pipe 106, the light introduced from the outside by the first guide pipe 106 may be prevented from flowing into the sensing block 204.

The explosive detection system according to the embodiment of the present invention may further include a first light blocking block 150 for blocking light that is externally introduced between the suction nozzle 100 and the sensor unit 108. In this case, the first guide pipe 106 may be formed through the first light blocking block 150 and may have a zigzag shape. The first guide pipe 106 having the zigzag shape may prevent the air that has flowed into the sensing block 204 from flowing toward the suction nozzle 100 and compress the air that has flowed into the first guide pipe 106, thereby removing moisture in the air.

As shown in FIG. 2, the sensor unit 108 may include a light source 200 that is composed of a laser diode and emits a predetermined light, for example, ultraviolet light, a lens 202 for collecting the light irradiated by the light source 200 into the sensing block 204, a seating portion 206 connected to the first connection pipe 118 and capable of receiving explosive particles in the air flowing through the first connection pipe 118, and a light receiving unit 208 that receives light corresponding to the reaction between the explosive particles and the detection material placed on the seating portion 206 and outputs the resulted signal of the light to the controller 130.

First, the light source 200 may be means for irradiating ultraviolet light, and examples thereof include LEDs, but the present invention may be not limited thereto.

The seating portion 206 may include a quartz made of a detecting material which is combined with explosive particles such as Nitro aromatic type of explosive materials to cause a change in light emission and extinction state represented by fluorescence change. Specifically, the seating portion 206 may maintain the fluorescence (light emission) state by the light incident from the light source 200. Thereafter, when the explosive particles are seated in the seating portion 206, the light may be changed from the light emission state by the light incident from the light source 200 to the extinction state.

The detection material may be an organic semiconductor compound consisting of a 1,1-disubstituted 4,5,8,9-bis (trypticin) metallaprolaurene compound represented by the following formula (I) capable of reacting with nitroaromatic explosive particles, however, the present invention is not limited thereto.

[Formula 1]

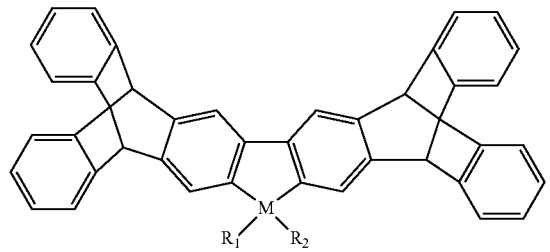

In the formula, M may be Si or Ge. If R1 and R2 are selected from the group consisting of H, alkylic group of C1 to C18, alkenyl group of C2 to C18, alkynyl group of C2 to C18, Substituent group or aromatic ring compound of C5 to C14, substituent group or aromatic ring compound containing a hetero atom (—NH—, —S—, —O—) of C3 to C10 or halogen atom, the substituents of R1 and R2 may be the same or different, respectively.

In addition, a predetermined adhesive coating material may be coated on the upper part of the seating portion 206 so that the explosive particles in the air flowing in the sensing block 204 may be easily adhered.

Meanwhile, a plurality of seating portions 206 having different lengths may be formed in the sensing block 204 according to the embodiment of the present invention. Specifically, a plurality of seating portions 206 may be formed in the sensing block so that the height thereof is sequentially lowered.

The light receiving unit 208 in the sensing block 204 according to the embodiment of the present invention may be a photodiode device connected to each of the seating portion 206 and capable of receiving light according to the light emission of the seating portion 206. The light receiving unit 208 in the sensing block 204 may receive light through the photodiode and then output the corresponding light sensing signal to the controller 130.

One side of the sensing block 204 may be connected to the first connection pipe 118 and the other side may be connected to the second connection pipe 120.

The sensor unit 108 may further include a shutter 210 for blocking the incidence of light between the lens 202 and the sensing block 204 and a shutter sensor 212 for sensing the operation state of the shutter 210. At this time, the shutter sensor 212 may apply a sensing signal corresponding to the operating state of the shutter 210 to the controller 130.

The process of detecting explosive particles by the sensor unit 108 as described above will be described below.

First, when ultraviolet light from the light source 200 in a state in which air is not introduced into the sensing block 204 or air in which no explosive particles are contained is introduced into the sensing block 204, the seating portion of the sensing block 204 may be maintained in a light emitting state. In this case, the light receiving unit 208 may receive light corresponding to the light emitted from the seating portion 206, and then output a light sensing signal corresponding to the received light to the controller 130.

Thereafter, when the air containing the explosive particles flows through the first connection pipe 118, the explosive particles may be seated on a predetermined portion of the seating portion 206. Accordingly, the detection material of the seating portion 206 may react with the explosive particles, and the detection material of the light emission state may be changed to the extinction state.

The light receiving unit 208 may receive the light corresponding to the light emission and extinction states for each of the seating portion 206, and provide the corresponding light sensing signal to the controller 130. Accordingly, the controller 130 may recognize that the explosive particles are detected in the air according to the extinction state of the seating portion 206.

Meanwhile, one side of the second connection pipe 120 may be connected to the sensing block 204, and the other side may be connected to the second guide pipe 110.

The second guide pipe 110 may be connected to the end of the connection nozzle 112 connected to the second connection pipe 120 at one side and connected to the suction force generation unit 114 at the other side.

The air introduced into the sensing block 204 by the suction force generated by the suction force generating unit 114 may be guided to the connecting nozzle 112 through the second connecting pipe 120 and the second guide pipe 110, and the air guided to the connection nozzle 112 may be discharged to the outside through the discharge port 20 formed at the end of the discharge nozzle 116.

The explosive detection system according to the embodiment of the present invention may further include a second light blocking block 160 formed between the sensor unit 108 and the suction force generation unit 114.

The second light blocking block 160 may block external light flowing through the suction force generating unit 114 and the discharge port 20. In this case, the second guide pipe 110 may be formed through the second light blocking block 160 and may have a zigzag shape.

The diameter of the portion of the second guide pipe 110 connected to the second connection pipe 120 may be smaller than the diameter of the other portion of the second guide pipe 110 connected to the connection nozzle 112. Accordingly, the air introduced into the sensing block 204 may be discharged through the discharge port 20 because the flow velocity is slow.

Meanwhile, the second guide pipe 110 may be arranged in a zigzag shape so as to have a width larger than the height of the sensing block 204, and may be connected to the second connection pipe 120. Through the structure of the second guide pipe 110, the light introduced from the outside by the first guide pipe 106 may be prevented from flowing into the sensing block 204.

The suction force generating unit 114 may be a means capable of generating a suction force for operating air under the control of the controller 130 and allowing the air to be sucked through the suction port 10, and examples thereof include a fan.

The suction force generating unit 114 may be connected to one end of the discharge nozzle 116 (the opposite end of the discharge port) and may be connected to the second guide pipe 110 through the connection nozzle 112. In other words, the suction force generating unit 114 may be connected to the suction nozzle 100 through the connection nozzle 112, the second guide pipe 110, the sensing block 204, the first connection pipe 118, so that the air including the explosive particles may be sucked through the suction port 10 of the suction nozzle 100.

The explosive detection system according to the embodiment of the present invention may further include a power supply unit 140 for supplying power to the sensor unit 108, the suction force generation unit 114, and the like.

The power supply unit 140 may supply power to each element in the sensor unit 108, for example, the light source 200, the light receiving unit 208, the shutter 210, and the suction power generation unit 114.

The controller 130 is a central processing unit for controlling overall functions of the explosive detection system and may control the operation states of the sensor unit 108 and the suction force generation unit 114. This will be described in detail as follows.

First, the controller 130 may control the suction force generation unit 114 based on the signals measured from the speed sensor 102 and the temperature and humidity sensor 104 to control the suction force of the air flowing through the suction port 10. Specifically, the controller 130 may acquire the flow velocity information of the air flowing through the suction port 10 based on the velocity measurement signal sensed by the velocity sensor 102, and generate a suction force when the flow velocity obtained is less than a predetermined threshold value, the suction force generated by the suction force generation unit 114 may be increased by controlling the power supplied to the unit 114. For example, when the suction force generating unit 114 is the fan, the operating speed of the fan may be increased to increase the suction force.

In addition, the controller 130 may acquire humidity information in the air based on the signal measured by the temperature and humidity sensor 104, and generate humidity information based on the humidity information obtained by the suction force generation unit 114 and the suction force may be controlled. Specifically, when the humidity of the air flowing into the suction nozzle 100 through the suction port 10 is equal to or greater than a predetermined threshold value, the controller 130 may control the power supplied to the suction force generating unit 114. For example, when the suction force generating unit 114 is the fan, the operating speed of the fan may be lowered to lower the suction force.

The operation of the explosive detection system having the above-described structure will be described below.

First, the controller 130 may control the power supply unit 140 to apply power to the suction force generation unit 114 so as to generate a predetermined suction force.

The suction force generated in this manner may be transmitted through the connection nozzle 112, the second guide pipe 110, the second connection pipe 120, the sensing block 204, the first connection pipe 118 and the first guide pipe 106 to the suction nozzle 100. The suction nozzle 100 may suck the air, that is, the air containing the explosive particles, through the suction port 10 according to the suction force, and introduce the air into the first guide pipe 106.

The first guide pipe 106 may provide the introduced air to the first connection pipe 118. At this time, the air introduced through the suction nozzle 100 due to the zigzag shape may be compressed to some extent. The air introduced into the first guide pipe 106 through this compression may be removed to some extent. The flow rate may then be increased by the outlet having a smaller diameter than the inlet of the first guide pipe 106 and may be discharged to the sensing block 204 of the sensor unit 108 through the first connection pipe 118.

The air introduced into the sensing block 204 may be retained to some extent by the shape of the second guide pipe 110. Specifically, the zigzag shape of the second guide pipe 110 and the narrowed inlet of the second guide pipe 110 may reduce the flow rate of air flowing into the second guide tube 110. Accordingly, the air introduced into the sensing block 204 may be slowly flowed into the connection nozzle 112 through the second guide pipe 110 connected to the second connection pipe 120, through the discharge port 20 of the discharge nozzle.

Meanwhile, the explosive particles in the air introduced into the sensing block 204 may be seated in the seating portion 206 of the sensing block 204.

Accordingly, the light irradiated by the light source 200 and incident through the lens 202 may be incident on the explosive particles seated on the seating portion 206.

Meanwhile, the explosive detection system may further include a configuration for providing various functions in addition to the above-described configuration. This will be described with reference to FIG. 3.

Figure 3:
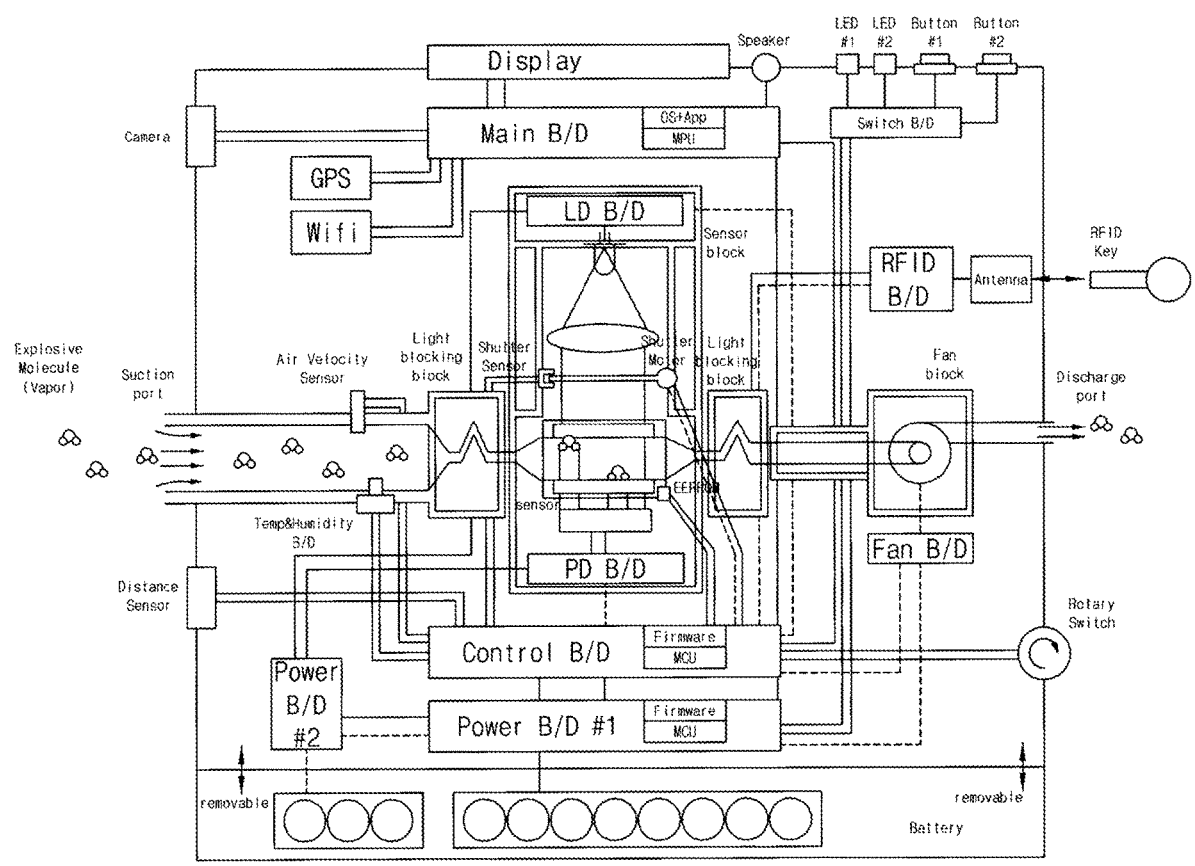
FIG. 3 is a structural view illustrating a detailed configuration of an explosive detection system according to another embodiment of the present invention.

FIG. 3 is a structural view illustrating a detailed configuration of an explosive detection system according to another embodiment of the present invention.

As shown in FIG. 3, the explosive detection system according to another embodiment of the present invention may include in addition to the components included in FIGS. 1 and 2, a GPS for acquiring position information of itself, modules, various types of operating systems (e.g., the Android operating system), and applications. The explosive detection system includes a main board capable of providing status information, detection result information, and control information through a display, a camera for capturing an external image, a distance sensor, an antenna for receiving an RFID key for recognizing a specific RFID, a plurality of LED elements for indicating the state of the explosive detection system, a state check unit capable of controlling the buttons, and a fan control unit for controlling the operation of the fan.

The explosive detection system may provide an interface, e.g., a removable interface, that can be coupled to an external battery to charge the power source 140. In this case, as the external battery is connected, the power source unit 140 may be charged by the external battery.

The foregoing is illustrative of embodiments and is not to be construed as limiting thereof. Although a few embodiments have been described, those skilled in the art will readily appreciate that many modifications are possible in the embodiments without materially departing from the novel teachings and advantages of the invention. Accordingly, all such modifications are intended to be included within the scope of the invention as defined in the claims. In the claims, means-plus-function clauses are intended to cover the structures described herein as performing the recited function and not only structural equivalents but also equivalent structures. Therefore, it is to be understood that the foregoing is illustrative of various embodiments and is not to be construed as limited to the specific embodiments disclosed, and that modifications to the disclosed embodiments, as well as other embodiments, are intended to be included within the scope of the appended claims.

What is claimed is:

1. An explosive detection system comprising:
    a suction nozzle having a suction port for introducing air containing explosive particles at one end thereof;
    a discharge nozzle having a discharge port for discharging air at one end thereof;
    a sensing block in which a detection material capable of detecting explosive particles in the air is disposed;
    a sensor unit for emitting light to the sensing block and outputting a sensing signal;
    a first guide pipe connected to other end of the suction nozzle and guiding the air introduced through the suction nozzle to the sensing block in which the detection material is disposed;
    a suction force generating unit formed at the other end of the discharge nozzle and to suck air through the suction port and to provide a suction force for sucking air into the sensing block and discharging the air to a discharge port formed at one end of the discharge nozzle;
    a second guide pipe formed between the sensing block and the suction force generating unit and discharging the air introduced into the sensing block by the suction force generated by the suction force generating unit to the discharge port of the discharge nozzle, and
    a controller for determining whether explosive particles are present in the air using the sensing signal,
    wherein the explosive detection system further includes a first connection pipe having one end connected to the sensing block and other end connected to the first guide pipe,
    wherein a diameter of a portion connected to the suction nozzle in the first guide pipe is larger than a diameter of a portion connected to the first connection pipe,
    wherein the first guide pipe is formed in a zigzag shape so as to have a width larger than height of the sensing block,
    wherein the explosive detection system further includes a second connection pipe having one end connected to the sensing block and other end connected to the second guide pipe,
    wherein the second guide pipe is formed in a zigzag shape so as to have a width larger than the height of the sensing block.

2. The explosive detection system of claim 1, wherein the explosive detection system further includes a first light blocking block through which the first guide pipe passes, disposed between the suction nozzle and the sensor unit for blocking the introduction of external light into the sensing block.

3. The explosive detection system of claim 1, wherein the explosive detection system further includes a second light blocking block through which the second guide pipe passes, disposed between the suction force generating unit and the sensor unit for blocking the introduction of external light into the sensing block.

4. The explosive detection system of claim 1, wherein the sensor unit includes a light source for emitting light and a lens for collecting the light toward the sensing block, wherein the sensing block includes at least two seating portions that can receive the explosive particles and are emitted when the light is incident and are then extinguished as the explosive particles are seated, and a light receiving unit that receives light corresponding to the light emission or extinction state of each of the seating portions and provides the corresponding light sensing signal to the controller.

\* \* \* \* \*